(12) United States Patent
Kreeger et al.

(10) Patent No.: US 7,868,164 B2
(45) Date of Patent: Jan. 11, 2011

(54) CELLULOSE ETHERS

(75) Inventors: Russell L. Kreeger, Flemington, NJ (US); Shuiqin Zhou, Staten Island, NY (US)

(73) Assignee: Union Carbide Chemicals and Plastics Technology Corporation

( * ) Notice: Subject to any disclaimer, the term of this patent is extended or adjusted under 35 U.S.C. 154(b) by 443 days.

(21) Appl. No.: 10/552,598

(22) PCT Filed: May 27, 2004

(86) PCT No.: PCT/US2004/016788
§ 371 (c)(1),
(2), (4) Date: Oct. 7, 2005

(87) PCT Pub. No.: WO2005/000903
PCT Pub. Date: Jan. 6, 2005

(65) Prior Publication Data
US 2007/0031362 A1    Feb. 8, 2007

(51) Int. Cl.
*C08B 15/06*     (2006.01)
*C08B 11/193*    (2006.01)
*A61K 31/717*    (2006.01)
*C08B 11/00*     (2006.01)
*C07H 1/00*      (2006.01)

(52) U.S. Cl. .............................. 536/30; 536/43; 536/44; 536/124; 514/57

(58) Field of Classification Search ................... 536/31, 536/43, 44, 124, 30; 514/57
See application file for complete search history.

(56) References Cited

U.S. PATENT DOCUMENTS

| | | | |
|---|---|---|---|
| 3,472,840 A * | 10/1969 | Stone et al. | .................... 536/43 |
| 4,228,277 A | 10/1980 | Landoll | |
| 4,663,159 A | 5/1987 | Brode, II et al. | |
| 4,845,175 A | 7/1989 | Lo | |
| 5,407,919 A | 4/1995 | Brode et al. | |
| 6,372,901 B1 | 4/2002 | Partain, III et al. | |
| 6,489,274 B1 * | 12/2002 | LeGrow et al. | ............. 510/122 |

* cited by examiner

*Primary Examiner*—Shaojia Anna Jiang
*Assistant Examiner*—Everett White

(57) ABSTRACT

A cellulose ether which has from 4,000 to 10,000 anhydroglucose repeat units and is substituted with (a) on the average from 0.0003 to 0.08 moles, per mole of anhydroglucose unit, of a substituent comprising an alkyl or arylalkyl group having from 8 to 24 carbon atoms and (b) a substituent having the formula II wherein $R^5$, $R^6$ and $R^7$ each independently are —$CH_3$ or —$C_2H_5$, $R^8$ is —$CH_2$—CHOH—$CH_2$— or —$CH_2CH_2$, $A^{z-}$ is an anion, and z is 1, 2 or 3 is useful in hair and skin care compositions.

1 Claim, No Drawings

CELLULOSE ETHERS

FIELD OF THE INVENTION

The present invention relates to cellulose ethers comprising a hydrophobic substituent and a cationic substituent, their production and their use in personal care compositions.

BACKGROUND OF THE INVENTION

Cellulose ethers comprising a hydrophobic substituent and/or a cationic substituent have been known since many years.

U.S. Pat. No. 3,472,840 discloses quaternary nitrogen-containing cellulose ethers and their use as flocculents for paper pulp, coal dust or silica or clay or as a retention aid in the manufacture of paper.

U.S. Pat. No. 4,663,159 discloses hydrophobically substituted water-soluble cationic polysaccharides. The hydrophobic substituent is a quaternary substituent which contains nitrogen and an alkyl group of at least 8 carbon atoms. The water-soluble polysaccharides are typically hydroxyethyl celluloses which have on the average about 2 moles of hydroxyethyl substituent per mole of polysaccharide repeat unit. The disclosed hydroxyethyl celluloses have a molecular weight to provide a 2 weight percent Brookfield viscosity between 20 and 500 cps, which corresponds to about 400-1,600 anhydroglucose repeat units. The hydrophobically substituted water-soluble polysaccharides are useful in hair and skin treatment formulations, such as shampoos and hand lotions. However, it would be desirable to improve the substantivity of these polymers, that means the retention of the polymers at a solid surface, such as hair or skin, when aqueous compositions containing such polymers, are applied to hair or skin.

U.S. Pat. No. 5,407,919 discloses double substituted cationic cellulose ethers substituted with greater than 0.11 to 0.25 moles, per mole of anhydroglucose unit, of a hydrophobic substituent and with from 0.05 to 0.50 moles, per mole of anhydroglucose unit, of a cationic substituent. The cationic cellulose ethers have enhanced viscosity and foaming, but poor substantivity. Unfortunately, typical shampoo formulations containing these cationic cellulose ethers are very viscous, to the point of forming gels, which makes them impractical.

Accordingly, it would be desirable to provide new cellulose ethers which are useful in personal care compositions, such as hair or skin care compositions. It would be particularly desirable to provide new cellulose ethers which provide hair or skin care compositions with an optimized viscosity and/or good substantivity. It is a preferred object of the present invention to provide new cellulose ethers which are useful for preparing hair care compositions with good wet and dry combability and/or a good wet and dry feel. It is another preferred object of the present invention to provide new cellulose ether derivatives for preparing skin care compositions which comprise a moisturizing agent, particularly for preparing skin care compositions which leave a high level of moisturizing agent, such as sunflower seed oil on the skin.

SUMMARY OF THE INVENTION

One aspect of the present invention is a cellulose ether which has from 4,000 to 10,000 anhydroglucose repeat units and which is substituted with (a) on the average from 0.0003 to 0.08 moles, per mole of anhydroglucose unit, of a substituent comprising an alkyl or arylalkyl group having from 8 to 24 carbon atoms and (b) a substituent having the formula II $$[R^5R^6R^7R^8N^+](A^{z-})_{1/z} \quad (II)$$

wherein
$R^5$, $R^6$ and $R^7$ each independently are —CH$_3$ or —C$_2$H$_5$,
$R^8$ is —CH$_2$—CHOH—CH$_2$— or —CH$_2$CH$_2$—
$A^{z-}$ is an anion, and
z is 1, 2 or 3.

Another aspect of the present invention is a process for producing the above-mentioned cellulose ether. The process comprises the step of reacting a cellulose ether having from 4,000 to 10,000 anhydroglucose repeat units with (a) a compound comprising an alkyl or arylalkyl group having from 8 to 24 carbon atoms and being selected from the group consisting of glycidylethers, alpha-olefin epoxides, alkylhalides compounds of formula Ia and mixtures thereof $$R^1R^2R^{10}R^4N^+(A^{z-})_{1/z} \quad (Ia)$$

wherein
$R^1$ and $R^2$ each independently are —CH$_3$ or —C$_2$H$_5$,
$R^4$ is an alkyl or arylalkyl group having from 8 to 24 carbon atoms,

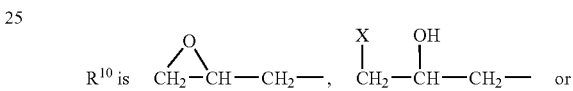

$A^{z-}$ is an anion, and
z is 1, 2 or 3; and
(b) a compound of formula IIa $$[R^5R^6R^7R^9N^+](A^{z-})_{1/z} \quad (IIa)$$

wherein
$R^5$, $R^6$ and $R^7$ each independently are —CH$_3$ or —C$_2$H$_5$,

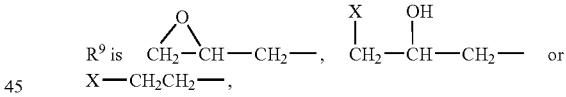

$A^{z-}$ is an anion, and
z is 1, 2 or 3.

Yet another aspect of the present invention is a personal care composition, such as a hair or skin care composition, which comprises the above-mentioned cellulose ether.

DETAILED DESCRIPTION OF THE INVENTION

Cellulose ethers suitable for use in accordance with the present invention include etherified derivatives of cellulose. Typical cellulose ethers include for example, hydroxyethyl cellulose, hydroxypropyl cellulose, methyl cellulose, hydroxypropyl methyl cellulose, hydroxyethyl methyl cellulose or hydroxyethyl carboxylmethyl cellulose. Preferred cellulose ethers include hydroxyethyl cellulose and hydroxypropyl cellulose. The most preferred cellulose ethers suitable for use in accordance with the present invention comprise hydroxyethyl groups. Preferably, these cellulose ethers have an M.S. (hydroxyethyl) of from 1.0 to 3.0, more preferably from 1.5 to 2.5. The M.S. (hydroxyethyl) designates the average number of moles of hydroxyethyl groups which have been attached by an ether linkage per mole of anhydroglucose unit. The cellulose ethers have at least 4,000 anhydroglucose repeat units, preferably at least 4,500 anhydroglucose repeat units, more preferably at least 5,000 anhydroglucose repeat units, and most preferably at least 6,000 anhydroglucose repeat units. The cellulose ethers have up to 10,000 anhydroglucose repeat units, preferably up to 9,000 anhydroglucose repeat units and most preferably up to 8,000 anhydroglucose repeat units. Such cellulose ethers are readily commercially available. Alternatively, such cellulose ethers can be prepared from cellulose by methods known to those skilled in the art.

The cellulose ether derivatives of the present invention are cellulose ethers which are substituted with a hydrophobic substituent (a) and a cationic substituent (b) as described below.

Hydrophobic substituents (a) suitable for use in accordance with the present invention comprise an alkyl or arylalkyl group having from 8 to 24 carbon atoms, preferably from 10 to 24 carbon atoms, more preferably from 12 to 18 carbon atoms, and most preferably 12 to 15 carbon atoms. As used herein the term "arylalkyl group" means a group containing both aromatic and aliphatic structures. The most preferred aliphatic hydrophobic substituent is the dodecyl group, which is most preferably straight-chained. The hydrophobic substituent is typically cationic or non-ionic. Many hydrophobe-containing reagents suitable for use as hydrophobic substituents are commercially available. In addition, methods for preparing such hydrophobe-containing reagents, as well as methods for derivatizing cellulose ethers to comprise such hydrophobic substituents, are known to those skilled in the art. Note for example, U.S. Pat. No. 4,228,277 issued Oct. 14, 1980, U.S. Pat. No. 4,663,159, issued May 5, 1987 and U.S. Pat. No. 4,845,175, issued Jul. 4, 1989.

A preferred hydrophobic substituent (a) suitable for use in accordance with the present invention has the formula (I)

$$R^1R^2R^3R^4N^+(A^{z-})_{1/z} \qquad (I)$$

wherein
R$^1$ and R$^2$ each independently are —CH$_3$ or —C$_2$H$_5$,
R$^3$ is —CH$_2$—CHOH—CH$_2$— or —CH$_2$CH$_2$—
R$^4$ is an alkyl or arylalkyl group having from 8 to 24 carbon atoms, and
A$^{z-}$ is an anion, and
z is 1, 2 or 3.

Preferably, R$^1$ and more preferably, both R$^1$ and R$^2$ are —CH$_3$. Preferably, R$^3$ is —CH$_2$—CHOH—CH$_2$—. Preferably, R$^4$ is —C$_n$H$_{(2n+1)}$, where n is from 8 to 24, more preferably from 10 to 18, most preferably 12. A$^{z-}$ is an anion with the valency of z, such as phosphate, nitrate, sulfate or halide. Chloride is the most preferred ion. Z is preferably 1 or 2, more preferably 1. The most preferred hydrophobic substituents (a) are those wherein two or more, preferably each of R$^1$, R$^2$, R$^3$, R$^4$, A$^{z-}$ and z have the mentioned preferred meanings.

Other preferred hydrophobic substituents include those derived from hydrophobe-containing reagents comprising alkyl or arylalkyl groups having from 8 to 24 carbon atoms, preferably from 10 to 24 carbon atoms, more preferably from 12 to 18 carbon atoms, and most preferably 12 to 15 carbon atoms. Preferred are glycidyl ethers, such as nonylphenyl glycidyl ether or dodecylphenyl glycidyl ether; or alpha-olefin epoxides, such as 1,2-epoxy hexadecane and their respective chlorohydrins, or alkyl halides, e.g., dodecyl bromide, and mixtures thereof.

The average substitution level of the substituent (a) is at least 0.0003, preferably at least 0.0005 moles per mole of anhydroglucose unit and up to 0.08, preferably up to 0.07, and most preferably up to 0.05 moles per mole of anhydroglucose unit. More than one particular hydrophobic substituent can be substituted onto the cellulose ether provided that the total substitution level is within the ranges set forth above.

The cationic substituent (b) suitable for use in accordance with the present invention has the formula II

$$[R^5R^6R^7R^8N^+](A^{z-})_{1/z} \qquad (II)$$

wherein
R$^5$, R$^6$ and R$^7$ each independently are —CH$_3$ or —C$_2$H$_5$,
R$^8$ is —CH$_2$—CHOH—CH$_2$— or —CH$_2$CH$_2$—
A$^{z-}$ is an anion, and
z is 1, 2 or 3.

Preferably, R$^5$ is —CH$_3$. More preferably, R$^5$, R$^6$ and R$^7$ are —CH$_3$. Preferably, R$^8$ is —CH$_2$—CHOH—CH$_2$—. A$^{z-}$ is an anion with the valency of z, such as phosphate, nitrate, sulfate or halide. Chloride is the most preferred ion. Z is preferably 1 or 2, more preferably 1. The most preferred cationic substituents (b) are those wherein two or more, preferably each of R$^5$, R$^6$, R$^7$, R$^8$, A$^{z-}$ and z have the mentioned preferred meanings.

Methods for preparing cationic substituents (b) such as described above, as well as methods for derivatizing cellulose ethers to contain such cationic substituents, are known to those skilled in the art. Note for example, U.S. Pat. No. 4,663,159 issued May 5, 1987.

The average substitution level of the cationic substituent (b) is generally from about 0.02 to about 0.9 moles, preferably from about 0.05 to about 0.8 moles, more preferably from about 0.1 to about 0.6 moles, most preferably from 0.15 to 0.35 moles of the substituent (b), per mole of anhydroglucose unit. More than one particular cationic substituent (b) can be substituted onto the cellulose ether, but the total substitution level is preferably within the ranges set forth above.

The average weight percent of nitrogen per anhydroglucose repeat unit is preferably from about 0.2 to about 3.5 percent, more preferably from about 0.5 to about 2.5 percent, most preferably from about 0.5 to about 2.0 percent.

The most preferred cellulose ethers of the present invention comprise a preferred substituent (a) and a preferred substituent (b) as described above in combination, preferably in the preferred weight ranges disclosed above.

The cellulose ether derivatives of the present invention are typically water-soluble. As used herein, the term "water-soluble" means that at least 1 gram, and preferably at least 2 grams of the cellulose ether derivative are soluble in 100 grams of distilled water at 25° C. and 1 atmosphere. The extent of water-solubility can be varied by adjusting the extent of ether substitution on the cellulose ether and by adjusting the substitution level of the hydrophobic substituent and the cationic substituent. Techniques for varying the water solubility of cellulose ethers are known to those skilled in the art.

The cellulose ether derivatives of the present invention preferably have a viscosity of from 1,500 to 350,000 mPa·s, more preferably from 2,000 to 150,000 mPa·s, most preferably from 50,000 to 90,000 mPa·s, measured as a 2 weight percent aqueous solution at 25° C. with a Brookfield viscosimeter.

The cellulose ether derivatives of the present invention are produced by reacting a cellulose ether having from 4,000 to 10,000 anhydroglucose repeat units with (a) a compound which comprises an alkyl or arylalkyl group having from 8 to 24 carbon atoms and which is a glycidyl ether, an alpha-olefin epoxide, an alkyl halide, a compound of formula Ia below or a mixture thereof:

wherein $R^1, R^2, R^4, A^{z-}$ and z have the above-mentioned meanings and

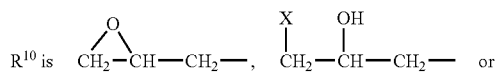

(b) a compound of formula IIa

wherein $R^5, R^6, R^7, A^{z-}$ and z have the above-mentioned meanings and

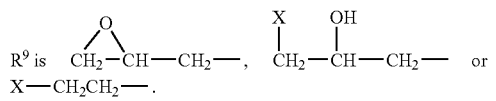

The compounds (a) and (b) can be reacted with the cellulose ether having from 4,000 to 10,000 anhydroglucose repeat units in any order. That is, the compound (a) can be reacted with the cellulose ether prior to, subsequent to, or simultaneously with the compound (b) in a known manner. Preferably, the reaction is carried as described in U.S. Pat. No. 5,407,919 while adapting the molar ratio between the cellulose ether and the compounds (a) and (b) to the desired substitution levels. Preferably, the molar ratio between the compound (a) and the anhydroglucose units of the cellulose ether is from 0.002 to 0.4, more preferably from 0.02 to 0.2. Preferably, the molar ratio between the compound (b) and the anhydroglucose units of the cellulose ether is from 0.1 to 2.0, more preferably from 0.3 to 0.7.

The cellulose ether derivatives of the present invention have a variety of end-use applications, such as, for example, industrial applications and household and personal care applications. Typical industrial applications include, for example, use as viscosity adjusters or suspension aids. Typical household and personal care applications include, for example, pharmaceutical and cosmetic compositions, such as contraceptive compositions, condom lubricants, vaginal ointments, douches, ophthalmic compositions, cleansers, skin creams, lotions, soaps, shampoos or conditioners.

A preferred end-use application for cellulose ether derivatives of the present invention is as a component in a personal care composition which comprises the cellulose ether derivative and a personal care ingredient. As used herein, the term "personal care ingredient" includes, but is not limited to, active ingredients, for example vitamins, silicone oils, sun screens, as well as solvents, diluents and adjuvants such as water, ethyl alcohol, isopropyl alcohol, higher alcohols, glycerin, propylene glycol, sorbitol, preservatives, surfactants, menthol, eucalyptus oil, other essential oils, fragrances or viscosity adjusters. Such personal care ingredients are commercially available and known to those skilled in the art.

The most preferred end-use application for cellulose ether derivatives of the present invention is as a component in hair or skin care compositions, such as shampoos, conditioners, hand or body lotions, soaps, and body wash formulations.

The amount of the cellulose ether derivatives present in the personal care composition will vary depending upon the particular composition. Typically, however, the personal cafe composition will comprise from about 0.05 to 5 weight percent, more preferably from about 0.1 to 1 weight percent of the cellulose ether derivative of the present invention, based on the total weight of the personal care composition.

Quite surprisingly, it has been found that at least the preferred cellulose ether derivatives of the present invention generally provide improved wet comb-ability, improved wet and dry feel, improved silicone deposition ability and/or improved polymer substantivity, as compared with cationic cellulose ether derivatives which do not contain a hydrophobic substituent and the number of anhydroglucose repeat units as described herein.

It has also been found that the cellulose ether derivatives of the present invention are very useful in skin care compositions, such as hand or body lotions, soaps, and body wash formulations. Skin care compositions commonly comprise skin moisturizing agents, such as sunflower seed oil. It is highly desirable that much of the moisturizing agent remains on the skin after it has been treated with the skin care composition. It has been found that at least the preferred cellulose ether derivatives of the present invention are very effective in the production of skin care compositions which provide a high deposition of the moisturizing agent, such as sunflower seed oil on the skin.

The present invention is illustrated by the following examples which are not to be construed to limit the scope of the invention. Unless otherwise indicated, all parts and percentages are by weight.

EXAMPLES

The molecular weights of the hydroxyethyl celluloses below are given as viscosities measured as a 1 or 2 weight percent aqueous solution at 25° C. using a Brookfield LTV viscometer.

The following materials are used in the Examples:

HEC-1: A hydroxyethyl cellulose having a viscosity of 5,700 cps (mPa·s) (1 percent), about 7000 to 8000 anhydroglucose repeat units and an average number of moles of hydroxyethyl groups per mole of anhydroglucose unit, designated as M.S.(hydroxyethyl), of about 2.2.

HEC-2: A hydroxyethyl cellulose having a viscosity of 2,400 cps (mPa·s) (1 percent), about 6500 to 7000 anhydroglucose repeat units and an M.S. (hydroxyethyl) of about 2.2.

HEC-3: A hydroxyethyl cellulose having a viscosity of 5,000 cps (mPa·s) (2 percent), about 2500 to 3500 anhydroglucose repeat units and an M.S. (hydroxyethyl) of about 2.2.

HEC-4: A partially water-soluble hydroxyethyl cellulose having a viscosity of 1400 cps (mPa·s) (1 percent), about 7000 to 8000 anhydroglucose repeat units and an M.S. (hydroxyethyl) of about 1.4.

HEC-5: A hydroxyethyl cellulose having a viscosity of about 700 cps (mPa·s) (2 percent), about 2500 to 3500 anhydroglucose repeat units and an M.S. (hydroxyethyl) of about 1.5.

Q151: A 70 weight percent aqueous solution of 2,3-epoxypropyltrimethyl ammonium chloride, commercially available from Degussa Corporation as QUAB™ 151.

Q342: A 40 weight percent aqueous solution of 3-chloro-2-hydroxypropyldodecyldimethyl ammonium chloride, commercially available from Degussa Corporation as QUAB™ 342.

NaOH: A 25 weight percent aqueous solution of sodium hydroxide.

IPA: Isopropyl alcohol.

The properties of the cellulose ether derivatives of the present invention are measured as follows:

Nitrogen content, percent N: The average weight percent of nitrogen per anhydroglucose repeat unit is determined analytically by using an automated Bucbi Kjeldahl distillation unit and titrating with an automated titrimeter.

The average number of moles of the hydrophobic substituent (a) per mole of anhydroglucose unit is designated as hydrophobic substitution (HS). According to one method the HS is measured using nuclear magnetic resonance (1H-NMR, 400 MHz, sodium trimethylsilyl propionate as a standard and deuterium oxide as a solvent at room temperature).

According to another method the HS is calculated based on a determination of the reaction efficiency of Q342 in reference reactions carried out under the same reaction conditions as described in Examples 1-21 below, but without adding Q151. The percent nitrogen in the resulting cellulose ether derivative which only contains 2-hydroxypropyldodecyldimethyl ammonium chloride as hydrophobic substituent (a), but no cationic substituent (b) is measured by the Kjeldahl method. From the weight percent of nitrogen and the weight of Q342 added to the reaction mixture per gram of HEC, the reaction efficiency of Q342 is calculated. The following data points (percent N/[Q342/g HEC]) are found: (0.03/0.039); (0.07/0.075); (0.11/0.15); (0.10/0.15); (0.18/0.29); (0.18/0.29); (0.25/0.44); (0.26/0.44); (0.38/0.58); (0.40/0.72); and (0.48/0.84). A linear regression is made based on these data points. It is found that a linear correlation exists between the percent N and the Q342 added to the reaction mixture per gram of HEC. From the percent nitrogen the hydrophobic substitution can be calculated. Also the Q342 efficiency can be calculated. Since in the reactions of Examples 1-21 most of the Q342 reacts completely before Q151 is added, the same reaction efficiency of Q342 is assumed in the reactions of Examples 1-21 as in the reference reactions which are carried out the absence of Q151. The accuracy of this method is controlled in a few examples by determining the HS by 1H-NMR. As illustrated by Table 2 below, the calculated HS based on efficiencies of the above-described reference reactions and the HS determined by 1H-NMR provide similar results.

The average number of moles of the cationic substituent (b) per mole of anhydroglucose unit is designated as cationic substitution (CS) and is measured using nuclear magnetic resonance (1H-NMR, 400 MHz, sodium trimethylsilyl propionate as a standard and deuterium oxide as a solvent at room temperature) and/or by calculating the difference between the total nitrogen content and the nitrogen content due to the HS.

Viscosity 1 percent: The viscosity of a 1 weight percent aqueous solution at 25° C. is measured using a Brookfield LTV viscometer at 30 rpm (revolutions per minute) and using an appropriate sized spindle listed in Table 1 below.

Viscosity 2 percent: The viscosity of a 2 weight percent aqueous solution at 25° C. is measured using a Brookfield LTV viscometer using spindle No. 4 at the rpm listed in Table 2 below.

A1. Preparation of the Hydroxyethyl Cellulose of Comparative Example A

A reaction vessel equipped with a stirrer, condenser, addition funnels, and nitrogen supply is charged with 41.6 g, on a pure basis, of hydroxyethyl cellulose (HEC) listed in Table 2 below, and with isopropyl alcohol and water in the amounts listed in Table 1 below. After purging with nitrogen, a 25 percent aqueous sodium hydroxide solution is added. The weight of sodium hydroxide, calculated as pure product, is listed in Table 1 below. After stirring for 30 minutes, Q151 is added. Its weight, calculated as undiluted 2,3 epoxypropyltrimethyl ammonium chloride is listed in Table 1 below. The reaction mixture is heated to 55° C. and held there for 120 minutes. After heating, the reaction mixture is cooled and neutralized by adding 2.4 g of acetic acid.

The reaction slurry is filtered and washed once with 400 g of 10 percent aqueous isopropyl alcohol, once with 400 g of 5 percent aqueous isopropyl alcohol, and once with 300 g of anhydrous isopropyl alcohol, and once with 200 g of anhydrous isopropyl alcohol containing 10 ml of 40 percent aqueous glyoxal and 10 ml of acetic acid. After drying under vacuum with low heat, 47 g of product containing about 3 percent volatiles is obtained.

A2. Preparation of the Hydroxyethyl Celluloses of Examples 1-21

A reaction vessel equipped with a stirrer, condenser, addition funnels, and nitrogen supply is charged with 41.6 g, on a pure basis, of hydroxyethyl cellulose (HEC) listed in Table 2 below, and with isopropyl alcohol and water in the amounts listed in Table 1 below. After purging with nitrogen, a 25 percent aqueous sodium hydroxide solution is added. The weight of sodium hydroxide, calculated as pure product, is listed in Table 1 below. After stirring for 30 minutes, Q342 is added. Its weight, calculated as undiluted 3-chloro-2-hydroxypropyldodecyldimethyl ammonium chloride is listed in Table 1 below. The reaction mixture is heated to 55° C., and held there for 60 to 90 minutes. While the reaction mixture is kept at 55° C., Q151 is added. Its weight, calculated as undiluted 2,3-epoxypropyltrimethyl ammonium chloride, is listed in Table 1 below. After heating for another 90 to 120 minutes (for a total cook out time of 180 minutes), the reaction mixture is cooled and neutralized wit 2.2 g acetic acid.

The reaction slurry is filtered and washed twice with 300 g of 10 percent aqueous isopropyl alcohol, once with 400 g of 10 percent aqueous isopropyl alcohol, and once with 300 g of anhydrous isopropyl alcohol, and once with 200 g of anhydrous isopropyl alcohol containing 10 ml of 40 percent aqueous glyoxal and 10 ml of acetic acid. After drying under vacuum with low heat, 47 g of product containing about 3 percent volatiles is obtained.

TABLE 1

Production of the cellulose ether derivatives

| (Comp.) Example | Grams NaOH | Grams Q151 | Grams Q342 | Grams IPA | Grams distilled water |
|---|---|---|---|---|---|
| A | 1.32 | 7.6 | 0 | 204 | 43.5 |
| 1 | 4.12 | 6.1 | 24 | 204 | 22 |
| 2 | 2.72 | 6.4 | 18 | 204 | 18 |
| 3 | 2.72 | 6.8 | 12 | 204 | 25 |
| 4 | 1.68 | 7.7 | 3.1 | 192 | 36 |
| 5 | 1.46 | 7.9 | 1.2 | 290 | 38 |
| 6 | 1.41 | 7.9 | 0.8 | 190 | 39 |
| 7 | 1.36 | 7.9 | 0.3 | 190 | 39 |
| 8 | 1.34 | 7.9 | 0.15 | 190 | 39 |
| 9 | 2.72 | 17 | 12 | 205 | 24 |
| 10 | 2.72 | 6.8 | 12 | 203 | 26 |
| 11 | 2.72 | 9.7 | 12 | 204 | 26 |
| 12 | 2.72 | 6.8 | 12 | 204 | 26 |
| 13 | 1.51 | 7.8 | 1.6 | 190 | 38 |
| 14 | 2.72 | 6.5 | 12 | 204 | 26 |
| 15 | 2.72 | 9.7 | 12 | 204 | 26 |

TABLE 1-continued

Production of the cellulose ether derivatives

| (Comp.) Example | Grams NaOH | Grams Q151 | Grams Q342 | Grams IPA | Grams distilled water |
|---|---|---|---|---|---|
| 16 | 2.72 | 6.5 | 12 | 204 | 26 |
| 17 | 1.51 | 7.8 | 1.6 | 190 | 37.5 |
| 18 | 2.04 | 7.3 | 6.2 | 204 | 38 |
| 19 | 1.41 | 19 | 0.8 | 192 | 37 |
| 20 | 1.51 | 19 | 1.6 | 192 | 37 |
| 21 | 1.68 | 18 | 3.1 | 194 | 34 |

TABLE 2

Properties of the produced cellulose ether derivatives

| (Comp.) Example | HEC | % N | HS* | HS** | CS | 1% viscosity | 2% viscosity |
|---|---|---|---|---|---|---|---|
| A | HEC-1 | 0.93 | 0.0 | 0.0 | 0.19 | 2460[1] | 40,000[4] |
| 1 | HEC-1 | 1.02 | 0.07 | 0.07 | 0.15 | 4500[2] | 330,000[5] |
| 2 | HEC-1 | 0.87 | 0.05 | 0.06 | 0.13 | 4200[2] | 152,000[6] |
| 3 | HEC-1 | 0.93 | 0.030 | 0.026 | 0.16 | 3070[1] | 58,000[6] |
| 4 | HEC-1 | 0.92 | 0.010 | 0.010 | 0.18 | 2980[1] | 69,000[6] |
| 5 | HEC-1 | 0.86 | 0.005 | 0.003 | 0.17 | 3500[2] | 68,000[6] |
| 6 | HEC-1 | 0.91 | 0.003 | —[10] | 0.18 | 3600[2] | 65,000[6] |
| 7 | HEC-1 | 0.86 | 0.001 | —[10] | 0.17 | 3600[2] | 57,000[6] |
| 8 | HEC-1 | 0.90 | 0.0005 | —[10] | 0.18 | 3600[2] | 62,000[6] |
| 9 | HEC-1 | 1.67 | 0.035 | —[10] | 0.34 | 2560[1] | 50,000[6] |
| 10 | HEC-2 | 0.90 | 0.030 | —[10] | 0.15 | 1600[2] | 17,000[7] |
| 11 | HEC-3 | 1.17 | 0.030 | 0.024 | 0.23 | 285[3] | 3,600[7] |
| 12 | HEC-3 | 0.92 | 0.030 | 0.022 | 0.17 | 340[3] | 5,000[7] |
| 13 | HEC-3 | 0.88 | 0.006 | 0.003 | 0.18 | —[10] | 3,400[7] |
| 14 | HEC-4 | 0.93 | 0.030 | —[10] | 0.14 | 6000[2] | 160,000[7] |
| 15 | HEC-5 | 1.17 | 0.030 | —[10] | 0.20 | 620[3] | 8,000[7] |
| 16 | HEC-5 | 0.96 | 0.030 | —[10] | 0.15 | 670[3] | 9,000[7] |
| 17 | HEC-1 | 0.91 | 0.006 | —[10] | 0.18 | 3000[2] | —[10] |
| 18 | HEC-1 | 0.87 | 0.02 | —[10] | 0.16 | 2700[2] | —[10] |
| 19 | HEC-1 | 1.79 | 0.003 | —[10] | 0.40 | 2000[2] | 26,000[4] |
| 20 | HEC-1 | 1.79 | 0.006 | —[10] | 0.40 | 2000[2] | 24,500[4] |
| 21 | HEC-1 | 1.71 | 0.010 | —[10] | 0.37 | 2200[2] | 28,000[4] |

*Calculated based on efficiencies of reference reactions as described above
**Determined by 1H-NMR
[1] Spindle No. 3
[2] Spindle No. 4
[3] Spindle No. 2
[4] 12 rpm
[5] 1.5 rpm
[6] 6 rpm
[7] 30 rpm
[10] not measured B. Wet Comb-Ability The wet combing force (WCF) is measured by using the load cell of an Instron Tensile Tester when a comb is pulled through a wet hair tress. The wet comb-ability of a shampoo formulation is calculated as follows in terms of the wet combing end-peak force (WCEPF) reduction of hair tress treated with a shampoo formulation containing a cellulose ether derivative listed in Tables 3-5 below, as compared to hair tress treated with a comparative formulation containing the same surfactant but no cellulose ether derivative: % WCEPF Reduction=$[(WCEPF_{control}-WCEPF_{shampooed})/WCEPF_{control}]\times 100$ where control means that the hair tress is treated by the same surfactant base as in the shampoo formulation but without cellulose ether derivative, and shampooed means that the hair tress is treated by the shampoo formulation comprising a certain amount of a cellulose ether derivative and the same surfactant base as used for control, respectively.

In a first comb-ability test the end-peak combing force reduction of an aqueous shampoo formulation A comprising 15.5 percent sodium laureth-2-sulfate (SLES), 2.6 percent disodium cocaamphodiacetate (DSCADA), 0.5 percent of a cellulose ether derivative listed in Table 3 below, and the remainder being water, is measured as indicated above and is listed in Table 3 below.

TABLE 3

Comb-ability of shampoo formulation A in relation to HS

| Cellulose ether of (Comp.) Example | HEC | % N | M.S. (hydroxyethyl) | HS | 2% viscosity | End Peak Force Reduction (%) |
|---|---|---|---|---|---|---|
| A | HEC-1 | 0.93 | 2.2 | 0.000 | 40,000 | 10 |
| 8 | HEC-1 | 0.90 | 2.2 | 0.0005 | 62,000 | 16 |
| 7 | HEC-1 | 0.86 | 2.2 | 0.001 | 57,000 | 56 |
| 6 | HEC-1 | 0.91 | 2.2 | 0.003 | 65,000 | 69 |
| 17 | HEC-1 | 0.91 | 2.2 | 0.006 | —*) | 83 |
| 4 | HEC-1 | 0.92 | 2.2 | 0.010 | 69,000 | 79 |
| 18 | HEC-1 | 0.87 | 2.2 | 0.02 | —*) | 72 |
| 3 | HEC-1 | 0.93 | 2.2 | 0.030 | 58,000 | 78 |
| 1**) | HEC-1 | 1.02 | 2.2 | 0.07 | 330,000 | 0 |

*)Not measured
**)Not directly comparable with the other examples because of the much higher viscosity In a second comb-ability test the end-peak combing force reduction of an aqueous shampoo formulation B comprising 14.3 percent sodium laureth-2-sulfate (SLES), 2 percent cocoamidopropyl betaine (CAPB), 0.5 percent of a cellulose ether derivative listed in Table 4 below, and the remainder being water, is measured as indicated above and listed in Table 4 below.

TABLE 4

Comb-ability of shampoo formulation B

| Cellulose ether of (Comp.) Example | HEC | % N | M.S. (hydroxyethyl) | HS | 2% viscosity | End Peak Force Reduction (%) |
|---|---|---|---|---|---|---|
| A | HEC-1 | 0.93 | 2.2 | 0.000 | 40,000 | 2 |
| 8 | HEC-1 | 0.90 | 2.2 | 0.0005 | 62,000 | 66 |
| 7 | HEC-1 | 0.86 | 2.2 | 0.001 | 57,000 | 64 |
| 6 | HEC-1 | 0.91 | 2.2 | 0.003 | 65,000 | 46 |
| 17 | HEC-1 | 0.91 | 2.2 | 0.006 | —*) | 11 |

*)Not measured

The results in Tables 3 and 4 illustrate that the wet comb-ability of a shampoo formulation can often be significantly improved by incorporating a cellulose ether derivative of the present invention into the shampoo formulation. The optimum level of substitution with the hydrophobic substituent (a) depends on the particular shampoo formulation.

In a further test, the wet comb-ability of shampoo formulation A which contains various cellulose ether derivatives of different molecular weights, expressed as viscosity of a 2 percent aqueous solution, is evaluated.

As illustrated by the results in Table 5 below, better comb-ability is achieved with cellulose ether derivatives of higher viscosity.

TABLE 5

Comb-ability of shampoo formulation A in relation to molecular weight

| Cellulose ether of (Comp.) Example | HEC | % N | M.S. (hydroxyethyl) | HS | 2% viscosity | End Peak Force Reduction (%) |
|---|---|---|---|---|---|---|
| 3 | HEC-1 | 0.93 | 2.2 | 0.030 | 58,000 | 78% |
| 10 | HEC-2 | 0.90 | 2.2 | 0.030 | 17,000 | 7% |
| 12 | HEC-3 | 0.92 | 2.2 | 0.030 | 5,000 | 0% |
| 11 | HEC-3 | 1.17 | 2.2 | 0.030 | 3,600 | 21% |
| 16 | HEC-5 | 0.96 | 1.5 | 0.030 | 9,000 | 0% |
| 15 | HEC-5 | 1.17 | 1.5 | 0.030 | 8,000 | 21% |
| 13 | HEC-3 | 0.88 | 2.2 | 0.006 | 3,400 | 6% |

In a further test, the wet comb-ability of shampoo formulation A which contains 0.5 percent or 0.3 percent of various cellulose ether derivatives with a relatively high nitrogen content is evaluated and listed in Table 6. The results in Table 6 illustrate that even with low molecular weight cellulose ether derivatives an improved comb-ability is achieved when the cellulose ether derivatives have a relatively high nitrogen content.

TABLE 6

Comb-ability of shampoo formulation A

| Cellulose ether of (Comp.) Example | HEC | % N | M.S. (hydroxyethyl) | HS | 2% viscosity | % cellulose ether in composition | End Peak Force Reduction (%) |
|---|---|---|---|---|---|---|---|
| B* | HEC-1 | 1.8 | 2.2 | 0 | 13,000 | 0.5% | 53 |
| 19 | HEC-1 | 1.79 | 2.2 | 0.003 | 26,000 | 0.5% | 73 |
| 20 | HEC-1 | 1.79 | 2.2 | 0.006 | 24,500 | 0.5% | 79 |
| 21 | HEC-1 | 1.71 | 2.2 | 0.01 | 28,000 | 0.5% | 82 |
| 9 | HEC-1 | 1.67 | 2.2 | 0.035 | 50,000 | 0.5% | 85 |
| B* | HEC-1 | 1.8 | 2.2 | 0 | 13,000 | 0.3% | 0 |
| 19 | HEC-1 | 1.79 | 2.2 | 0.003 | 26,000 | 0.3% | 43 |
| 20 | HEC-1 | 1.79 | 2.2 | 0.006 | 24,500 | 0.3% | 47 |
| 21 | HEC-1 | 1.71 | 2.2 | 0.01 | 28,000 | 0.3% | 35 |

*Comparative Example B is HEC-1 quaternized with 2,3-epoxypropyltrimethyl ammonium chloride and is commercially available under the trademark UCARE JR-30 M.

C.) Silicone Deposition Ability

An aqueous shampoo composition is prepared which comprises a) 0.25 percent of the cellulose ether derivative of Comparative Example A or of Example 17 respectively, b) 1 percent of a polydimethylsiloxane, commercially available from Dow Corning as 1664 Emulsion, c) 15.5 percent sodium laureth-2-sulfate (SLES) and d) 2.6 percent disodium cocaamphodiacetate (DSCADA), and the remainder being water.

The silicone deposition ability of a cellulose ether derivative is determined by measuring the amount of silicone conditioning ingredients deposited on hair from the cellulose ether-containing shampoo. The silicone ingredients are firstly extracted off from the hair by a solution comprising 50 volume percent of methylisobutylketone and 50 volume percent of toluene. An Atomic Absorption Spectrophotometer is used to detect the silicone concentration of the extracted sample solution, and then the micro-gram silicone per gram hair is calculated.

When hair is shampooed twice, the cellulose ether derivative of Example 17 having a HS of 0.006 can deliver about 30 percent more silicone than the cellulose ether derivative of Comparative Example A having an HS of 0.000. When hair is shampooed ten times, the cellulose ether derivative of Example 17 having a HS of 0.006 can deliver about 66 percent more silicone than the cellulose ether derivative of Comparative Example A having an HS of 0.000.

D) Polymer Substantivity and Build Up

Polymer Substantivity and Build up: The substantivity and build up on hair of a cellulose ether derivative are measured indirectly by detecting the amount of Lowacene Red 80 (trademark) dye molecules (from Jos. H. Lowenstein and Sons) bound by the cellulose ether derivative deposited on hair. The cationic cellulose ether derivatives can complex with the anionic dye of Lowacene Red 80 through both electrostatic and hydrophobic interactions, thus the amount of cellulose ether derivatives deposited on the shampoo-treated hair tress is proportional to the amount of dye molecules bound by the shampoo-treated hair. Typically, the shampoo-treated hair tresses, as described in the wet-combability test further above, are air-dried and then complexed with dye solution. After rinsing off the free dye molecules and squeezing off excess water, the dye molecules bound by the hair tresses are then extracted from the hair by a solution of 50 volume percent of isopropanol and 50 volume percent of de-ionized water. An UV Spectrometer is used to detect the dye concentration of the extracted solution at 533 nm. The micro-gram dye per gram hair is calculated.

When the shampoo composition comprises 0.5 percent of the cellulose ether derivative of Example 17 having a HS of 0.006, from 107 to 118 microgram dye per gram hair is detected on the hair that has been treated from 1 to 15 times with shampoo. When the shampoo composition comprises 0.5 percent of the cellulose ether derivative of Comparative Example A having a HS of 0.000, from 37 to 48 microgram dye per gram hair is detected on the hair that has been treated from 1 to 15 times with shampoo.

These results illustrate the higher substantivity of the cellulose ether derivatives of the present invention as compared to corresponding cellulose ether derivatives comprising a cationic substituent but no hydrophobic substituent. However, the increased amount of dye on the hair does not change with multiple shampoo treatments, illustrating that the cellulose ether derivatives of the present invention do not result in undesirable build up.

E. Preparation of the Hydroxyethyl Celluloses of Examples 22-24

A reaction vessel equipped with a stirrer, condenser, addition funnels, and nitrogen supply is charged with HEC-1 and with isopropyl alcohol and water in the amounts listed in Table 7 below. After purging with nitrogen, a 25 percent aqueous sodium hydroxide solution is added. The weight of sodium hydroxide, calculated as pure product, is listed in Table 7 below. After stirring for 30 minutes, Q342 is added. Its weight, calculated as undiluted 3-chloro-2-hydroxypropyl-dodecyldimethyl ammonium chloride is listed in Table 7 below. The reaction mixture is heated to 55° C. and held there for 60 to 90 minutes. While the reaction mixture is kept at 55° C., Q151 is added. Its weight, calculated as undiluted 2,3-epoxypropyltrimethyl ammonium chloride, is listed in Table 7 below. After heating for another 90 to 120 minutes (for a total cook out time of 180 minutes), the reaction mixture is cooled and neutralized wit 2.2 g acetic acid. The reaction slurry is filtered, washed and dried as described in Examples 1-21 above.

TABLE 7

Production of the cellulose ether derivatives 22–24

| Example | Grams NaOH | Grams Q151 | Grams Q342 | Grams IPA | Grams distilled water | Grams HEC |
|---|---|---|---|---|---|---|
| 22 | 2.73 | 16.0 | 1.3 | 360 | 77 | 80 |
| 23 | 1.77 | 9.8 | 1.5 | 226 | 47 | 50 |
| 24 | 3.15 | 15.4 | 4.8 | 365 | 72 | 80 |

TABLE 8

Properties of the produced cellulose ether derivatives 22–24

| (Comp.) Example | % N | HS* | CS | 1% viscosity | SFSO deposition (ppm) |
|---|---|---|---|---|---|
| 22 | 0.95 | 0.0025 | 0.20 | 2720 | 21.0 |
| 23 | 0.96 | 0.005 | 0.20 | 2700 | 19.9 |
| 24 | 0.96 | 0.010 | 0.20 | 2800 | 18.0 |

*Calculated based on efficiencies of reference reactions as described above

F. Evaluation Method for Sunflower Seed Oil Deposition from Body Wash Formulations Sunflower seed oil is commonly used as a skin moisturizing agent in body wash formulations. The study on deposition of sunflower seed oil is done on vitro skin. Sunflower seed oil is a natural triglyceride with different carbon chair lengths. The oil is derivatized to form methyl esters for Gas Chromatography analysis. Linoleic acid is the major component of sunflower seed oil and used as the indicator. The linoleic acid is measured by GC analysis. A fixed dimension of skin (3 cm×6 cm) is treated with 0.15 gram of a body wash formulation. The treatment includes 30 seconds of product application followed by 15 seconds of rinsing with water at a flow rate of 1 liter/minute. The body wash formulation comprises 11 percent sodium laurylether sulfate, 4 percent cocamidopropyl betaine, 1.5 percent sodium chloride, 15 percent sunflower seed oil and 0.5 percent of the cellulose ether listed in Table 8 and water making a total of 100 percent. Table 8 illustrates that body wash formulations comprising a cellulose ether of the present invention exhibit a good sun flower seed oil deposition.

What is claimed is:

1. A personal care composition, comprising:

hydroxyethyl cellulose ether having from 6,000 to 8,000 anhydroglucose repeat units, comprising on the average from 1.0 to 3.0 moles of hydroxyethyl groups, per mole of anhydroglucose unit, and being substituted with (a) on the average from 0.0005 to 0.05 moles, per mole of anhydroglucose unit, of a substituent of the formula I:

$$R^1R^2R^3R^4N^+(A^{z-})_{1/z} \qquad (I)$$

wherein
$R^1$ and $R^2$ each independently are —$CH_3$,
$R^3$ is —$CH_2$—$CHOH$—$CH_2$—,
$R^4$ is a dodecyl group, and
$A^{z-}$ is an anion, and
z is 1; and (b) on the average from 0.15 to 0.35 moles, per mole of anhydroglucose unit, of a substituent having the formula II:

$$[R^5R^6R^7R^8IC^+](A^{z-})_{1/z}, \qquad (II)$$

wherein
$R^5$, $R^6$ and $R^7$ each independently are —$CH_3$,
$R^8$ is —$CH_2$—$CHOH$—$CH_2$—,
$A^{z-}$ is an anion, and
z is 1; and a personal care ingredient, comprising eucalyptus oil or menthol.

* * * * *